United States Patent
Wagner et al.

(10) Patent No.: US 9,518,929 B2
(45) Date of Patent: Dec. 13, 2016

(54) ENGRAVED GEMSTONE VIEWER FOR PERSONAL COMMUNICATIONS DEVICES

(71) Applicant: GemEx Systems, Inc., Mequon, WI (US)

(72) Inventors: Randall Wagner, Mequon, WI (US); Kurt Schoeckert, Hartford, WI (US)

(73) Assignee: GemEx Systems, Inc., Mequon, WI (US)

( * ) Notice: Subject to any disclaimer, the term of this patent is extended or adjusted under 35 U.S.C. 154(b) by 0 days.

(21) Appl. No.: 14/723,046

(22) Filed: May 27, 2015

(65) Prior Publication Data

US 2015/0253255 A1 Sep. 10, 2015

Related U.S. Application Data

(63) Continuation-in-part of application No. 13/901,445, filed on May 23, 2013, now Pat. No. 9,213,187.
(Continued)

(51) Int. Cl.
*G02B 27/02* (2006.01)
*G02B 7/02* (2006.01)
(Continued)

(52) U.S. Cl.
CPC .............. *G01N 21/87* (2013.01); *G01N 21/03* (2013.01); *G02B 25/002* (2013.01);
(Continued)

(58) Field of Classification Search
CPC .... G02B 25/002; G02B 27/025; G02B 27/027
(Continued)

(56) References Cited

U.S. PATENT DOCUMENTS 6,731,439 B1  5/2004 Peachee
7,468,786 B2  12/2008 Wagner
(Continued)

FOREIGN PATENT DOCUMENTS

JP  WO 2004081653 A1 *  9/2004  ........... H04N 5/2254
WO  2012058641  5/2012

OTHER PUBLICATIONS

International Search Report for application PCT/US2013/042521, mailed Oct. 16, 2013.

*Primary Examiner* — William Choi
(74) *Attorney, Agent, or Firm* — Nicholas A. Kees; Godfrey & Kahn, S.C.

(57) ABSTRACT

A gemstone viewer for personal communications devices for viewing a gemstone surface on which has been formed an image or inscription such as an identification number. In one embodiment, the viewer is mounted to employ the camera and LED light source of the personal communications device. The viewer directs the light from the light source as a light beam along a path incident to the surface of the gemstone containing the inscription. The gemstone spectrally reflects the light beam along a path back toward and through a magnifying lens to the camera lens of the personal communications device thereby enhancing the magnifying properties of the camera lens to produce a viewable light image that reveals the inscription on the viewing screen of the personal communications device. In another embodiment, the viewer is aligned to the front facing camera of the personal communications device, and includes its own light source.

20 Claims, 15 Drawing Sheets

Related U.S. Application Data

(60) Provisional application No. 61/652,072, filed on May 25, 2012.

(51) Int. Cl.
*G01N 21/87* (2006.01)
*G01N 21/03* (2006.01)
*G02B 25/00* (2006.01)

(52) U.S. Cl.
CPC ......... *G02B 25/008* (2013.01); *G02B 27/024* (2013.01); *G02B 27/027* (2013.01); *G01N 2021/0339* (2013.01); *G01N 2201/0221* (2013.01); *G01N 2201/061* (2013.01); *G02B 7/026* (2013.01)

(58) Field of Classification Search
USPC .............................. 359/802, 811, 818, 819
See application file for complete search history.

(56) References Cited

U.S. PATENT DOCUMENTS

| | | |
|---|---|---|
| 8,035,807 B2 | 10/2011 | Wagner |
| 2007/0109529 A1 | 5/2007 | Wagner et al. |
| 2009/0093274 A1 | 4/2009 | Yamamoto |

\* cited by examiner

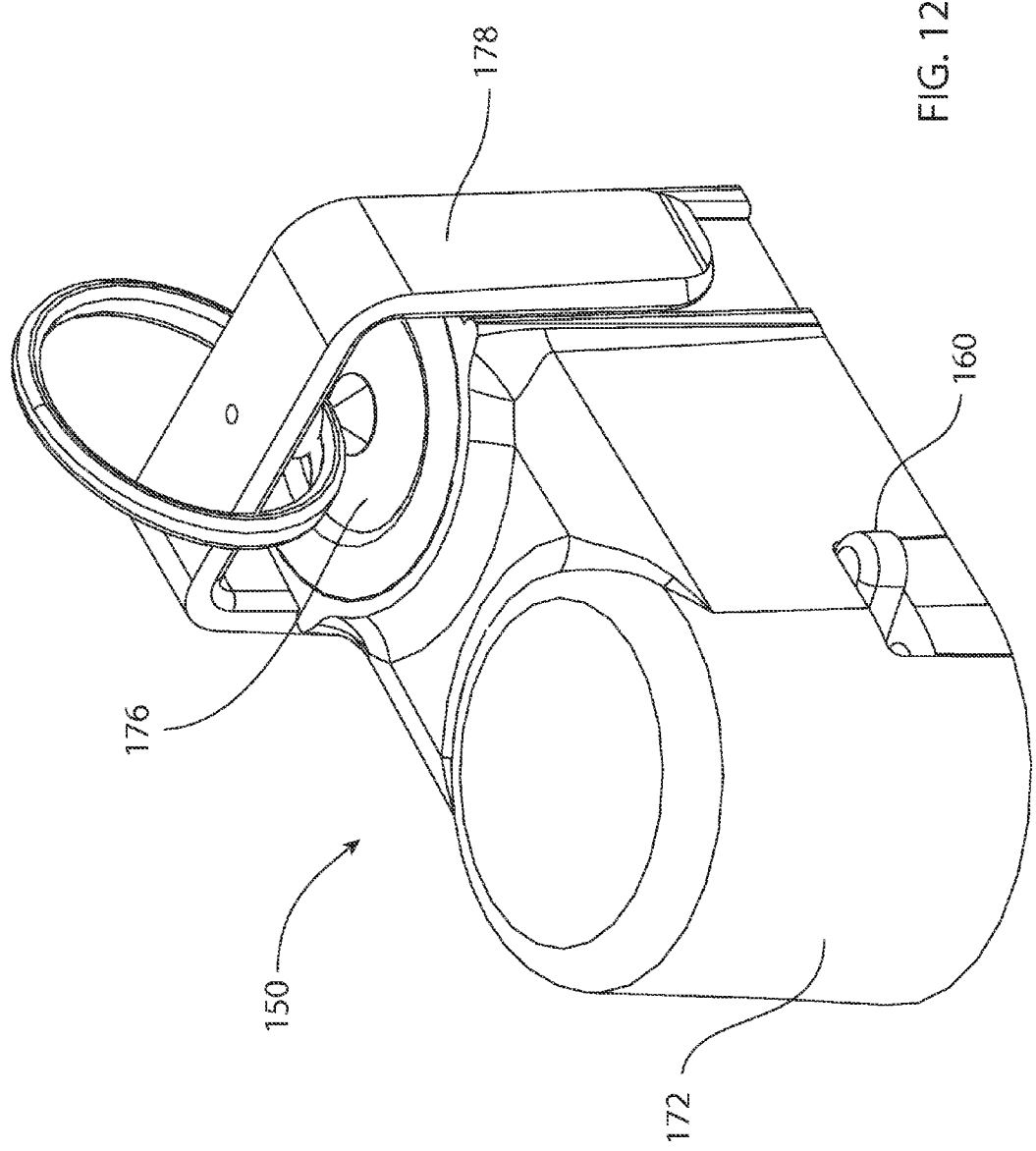

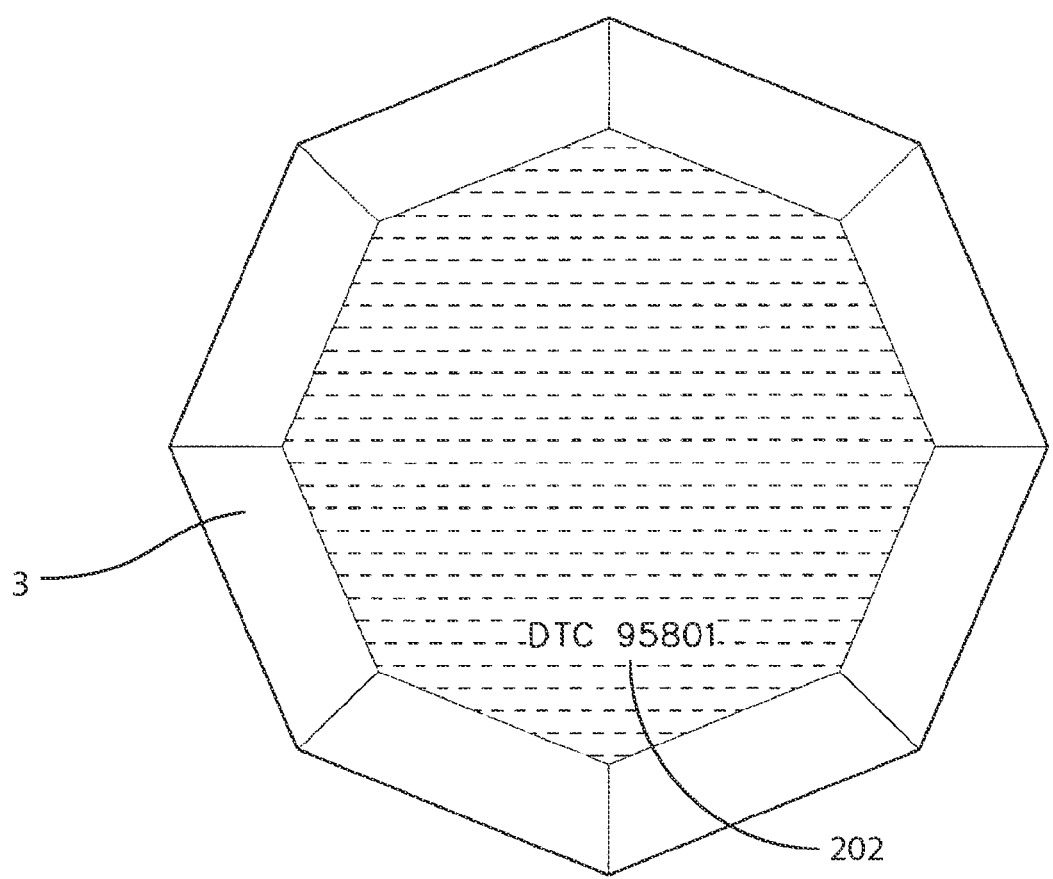

ENGRAVED GEMSTONE VIEWER FOR PERSONAL COMMUNICATIONS DEVICES

CROSS REFERENCE TO RELATED APPLICATIONS

This application is a continuation-in-part of U.S. patent application Ser. No. 13/901,445, filed May 23, 2013, and claims the benefit of U.S. Provisional Patent Application Ser. No. 61/652,072, filed May 25, 2012. All of the information disclosed in those applications is hereby incorporated herein by reference in its entirety.

BACKGROUND OF THE INVENTION

This invention relates to an apparatus for viewing a gemstone with an image or identification number etched into its surface.

It is known to etch a microscopic or nano-inscription on the table of the diamond using any one of a number of known techniques including plasma etching, ion beam, or lasers. The inscription is of such a small size as to be invisible to the naked eye. The inscription is nearly impossible to read even by a skilled jeweler using a common 10× loupe because the proper viewing angle is difficult to achieve. The images engraved, which can include individual characters (i.e., letters and/or numbers) such as an identification number, conventionally have a length of ranging from about 300 to 1200 microns. The inscription is typically etched to a depth of about 10 to 80 nanometers. The difficulty in viewing the inscription is accentuated by the translucent nature of diamonds and other gemstones, which allows light to pass through both the nano-inscroption polished area formed by the engraving process and the surrounding surface of the gemstone, (for example, the polished table facet).

The conventional method of viewing the inscription employed a high (65×, for example) magnification lens and camera with an electronic display screen to view the microscopic inscription. Such systems are expensive, cumbersome and complicated to use, which reduces the value of the inscription because most retailers and consumers do not have access to such equipment, and thus cannot see or make use of the inscription.

U.S. Pat. Nos. 7,468,786 and 8,035,807, which are incorporated by reference herein in their entirety, and invented by the same inventors as the present invention and owned by the same assignee, disclose a less expensive and more effective viewer (referred to hereinafter as an Engraved Gemstone Viewer) using the concept of illuminating the surface of the polished diamond in such a way as to create a spectral light reflection much like that of a mirror. The Engraved Gemstone Viewer is effective but lacks the convenience of being with the person at all times that engraving might be needed to be viewed, and further, lacks a way to memorize the image for later recall, comparison analysis, or remote communication of the information contained in the image.

The present invention is intended to provide solutions to these and other problems and improvements over the structures and methods described above.

SUMMARY OF THE INVENTION

The present invention provides a gemstone viewer for working with an electronic device having a camera lens. According to the invention, the gemstone viewer includes a base having an integral light source and a portal disposed in a bottom plane, one or more mirrors, a viewer lens, and a focusing glass or other optically clear structure, with the viewer lens positioned between the optically clear structure and the camera lens. The optically clear structure and the viewer lens are held at a sufficient distance from each other such that the camera lens is properly focused through the viewer lens to the surface of a gemstone when the surface of the gemstone is placed against the optically clear structure. The one or more mirrors are arranged to direct light from the integral light source off the surface of the gemstone to the camera lens.

In one variety, the base is removably secured to the electronic device. A removable retaining ring may hold the optically clear structure in place, and the optically clear structure is positioned to receive a gemstone thereon. The invention may also include a gemstone retention clip to secure a gemstone to the optically clear structure. The invention may also include a cover associated with the base, wherein the viewer lens is connected to the cover. The integral light source may be powered by a battery. The one or more mirrors may be attached to the base. A cover may be associated with the base, with the optically clear structure connected to the cover.

Other objects and advantages of the invention will become apparent hereinafter.

BRIEF DESCRIPTION OF THE DRAWINGS

FIG. 12 is another perspective view of the engraved gemstone viewer of FIG. 10.

FIG. 20 is an enlarged view of the light image produced by the viewer, showing an identification number.

DESCRIPTION OF THE PREFERRED EMBODIMENTS

Figure 1:
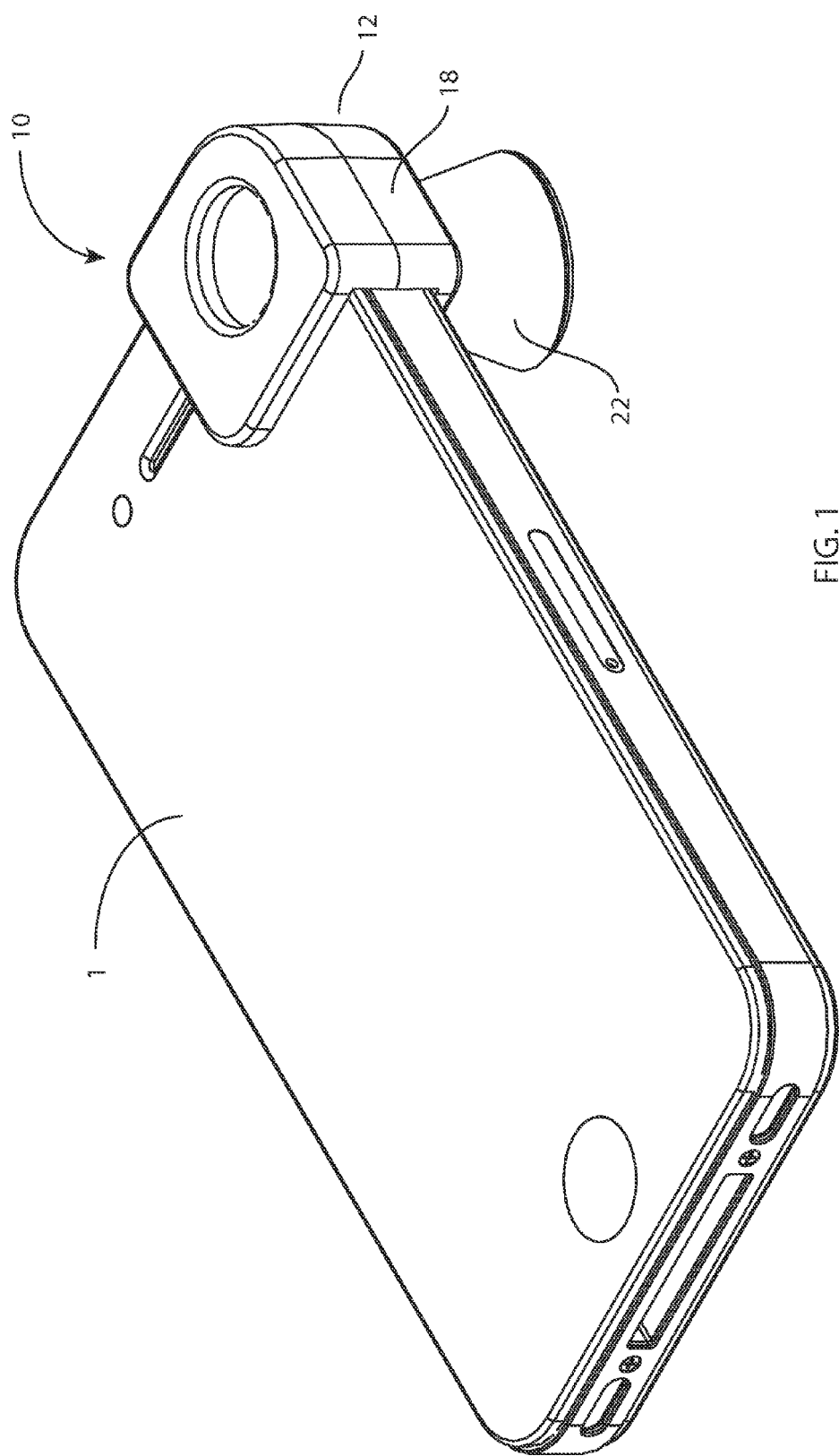
FIG. 1 is a perspective top-side view of the engraved gemstone viewer according to the present invention, mounted on an Apple® iPhone®.
Figure 2:
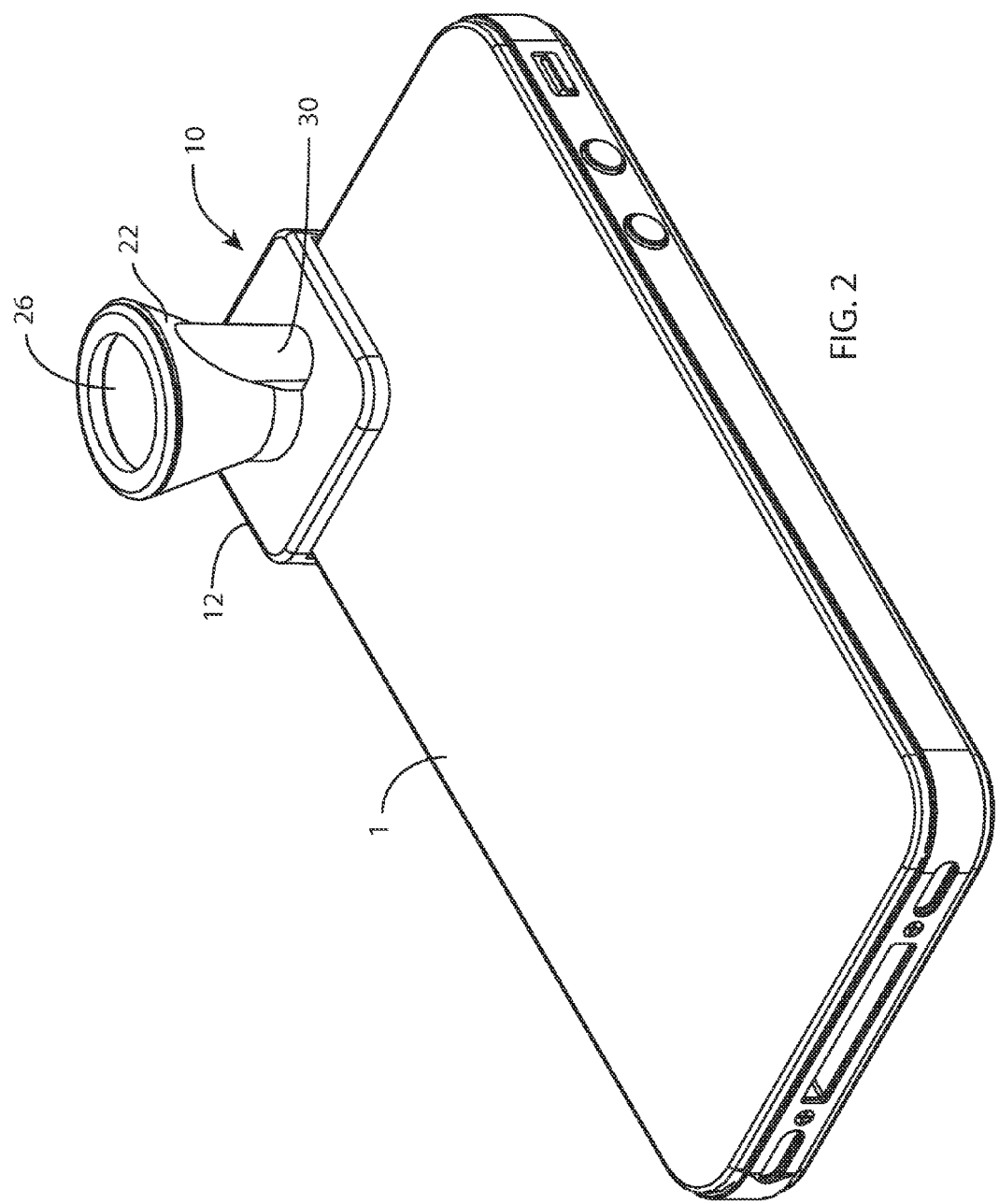
FIG. 2 is a perspective bottom-side view of the engraved gemstone viewer shown in FIG. 1, mounted on an Apple® iPhone®.
Figure 3:
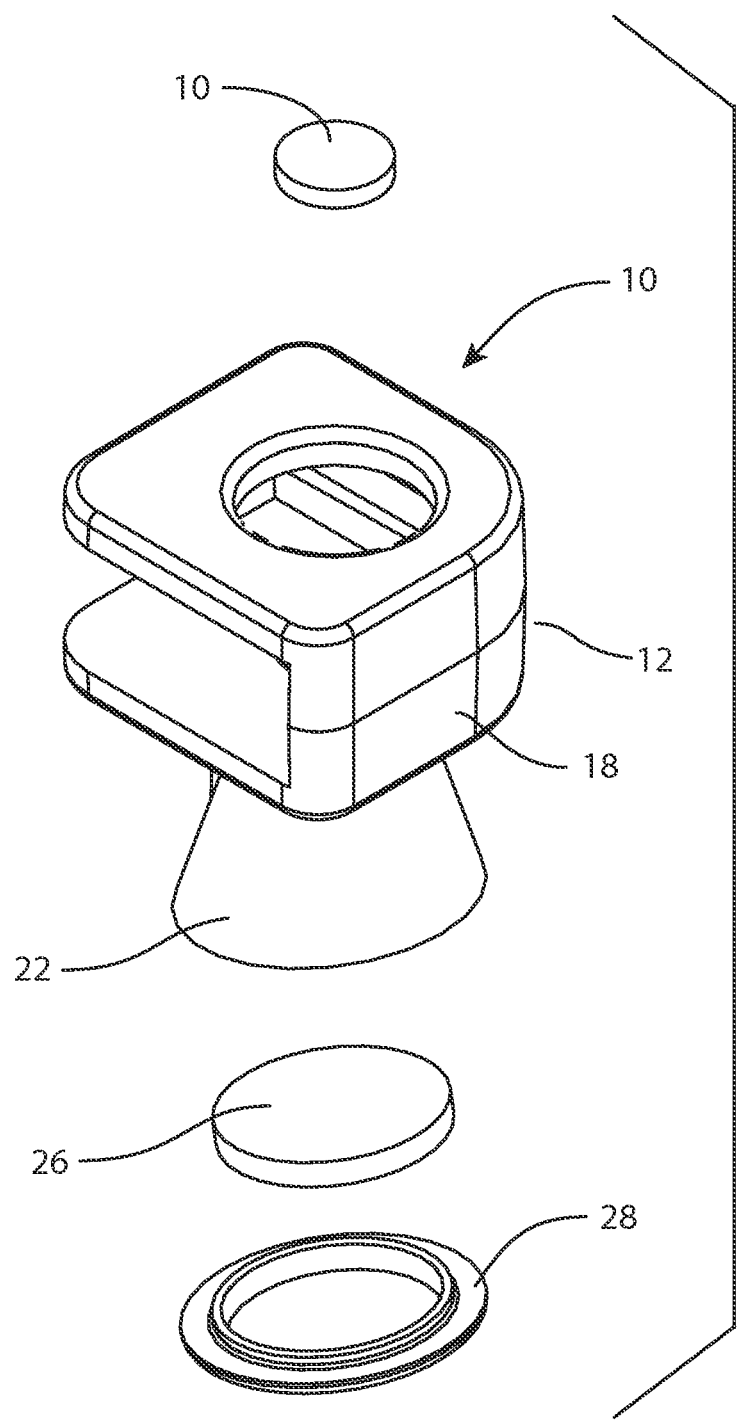
FIG. 3 is an exploded perspective view of the engraved gemstone viewer shown in FIG. 1.

The present invention generally relates to an engraved gemstone viewer 10 for personal communications device. The viewer 10 is generally shown in the drawing figures in the form of an embodiment specifically adapted to an Apple® iPhone®, although the viewer that is the subject of the invention is adaptable to be used with any smartphone, personal communications device or personal productivity device 1 with an integrated camera and a light source, such as an LED light, normally to provide photo lighting or "flash" capabilities. Such smartphone, personal communications or personal productivity devices could also include for example, a Samsung® Galaxy®, or a tablet-style computer such as an Apple® iPad®. According to the invention, the viewer 10 has a base 12 (shown generally roughly square in shape in the embodiment shown although many other shapes would function equally well) to receive the corner of a personal communications device 1 where the camera lens and light source are positioned on the back side of the personal communications device. In the embodiment shown, the base 12 has a top plane 14 and bottom plane 16 spaced apart by two adjoining side planes 18, 20, which preferably is formed unitarily but may as well be formed of parts and assembled. The base 12 is open on the opposing two adjoining sides so as to accommodate the thickness of the personal communications device 1 that is received through the two open sides. Preferably the top plane 14, bottom plane 16 and two side planes 18, 20 of the base 12 are precisely spaced so as to make frictional contact with the personal communications device 1, to thereby secure the viewer 10 to the personal communications device without applying additional pressure or mechanical means. In alternative embodiments of the viewer 10, the base 12 may have a different shape and size so as to correctly orient the device to receive a different model of smartphone or personal communications device, with the camera lens and light source in respectively different positions based on the positioning of the equipment in the personal communications device.

A viewer body 22, shown to have a funnel shape in this embodiment, is attached to or formed integrally with the bottom plane 16, and projects away from personal communications device 1. The viewer body 22 is a structure sized to accommodate a magnifying lens 24 generally at the level of the bottom plane 16, and generally coaxially aligned with but not contacting the lens 2 of the camera or body of the personal communications device 1. The bottom plane 16 is open to allow an unobstructed path for light to pass through the magnifying lens 24 to the lens 2 of the camera of the personal communications device 1. The magnifying lens 24 is of such a calibration as to visually enlarge objects in the view of the camera of the personal communications device 1 beyond that which is otherwise possible by the unaided lens of the camera itself.

Figure 5:
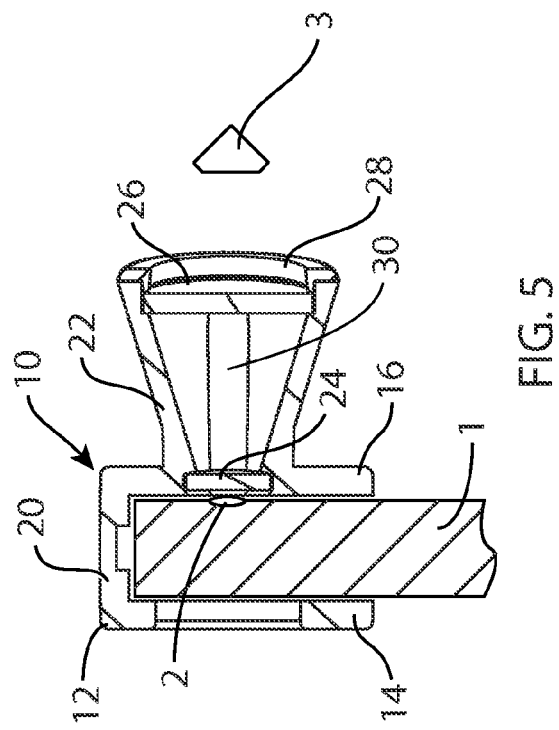
FIG. 5 is a side sectional view of the engraved gemstone viewer shown in FIG. 4, taken along line 5-5 of FIG. 4.
Figure 4:
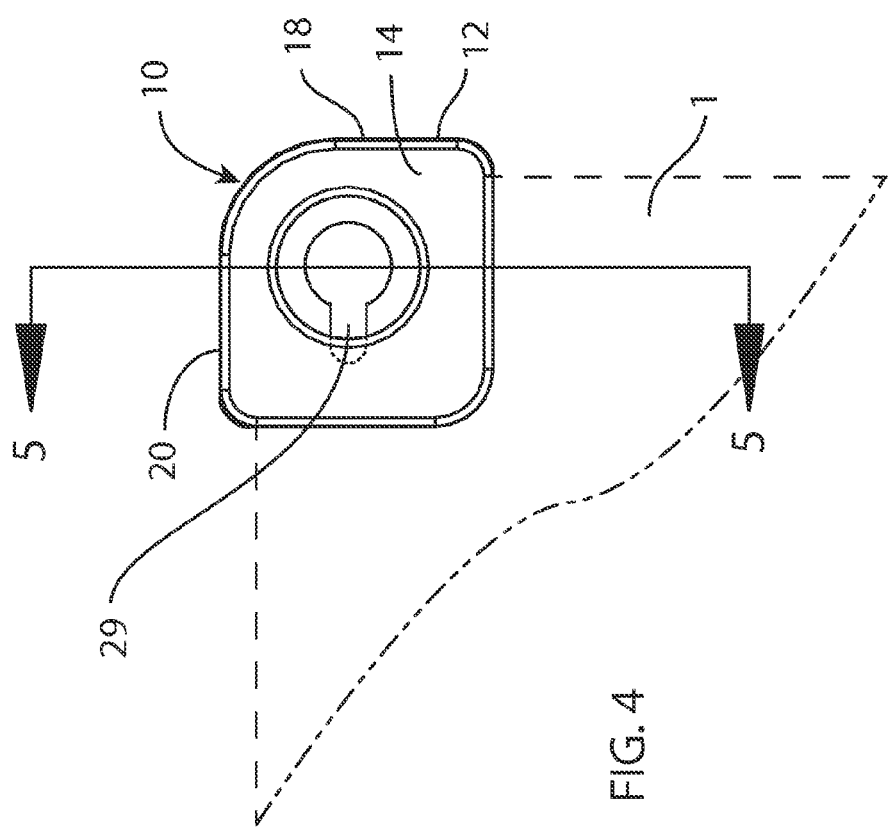
FIG. 4 is an enlarged top plan view of the engraved gemstone viewer shown in FIG. 1, shown with a portion of the personal communications device included, shown in phantom, for positioning purposes only.
Figure 7:
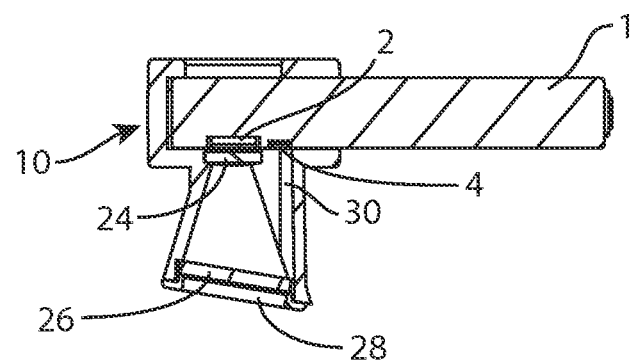
FIG. 7 is a side sectional view of the engraved gemstone viewer for smartphones shown in FIG. 6, taken along line 7-7 of FIG. 6.
Figure 6:
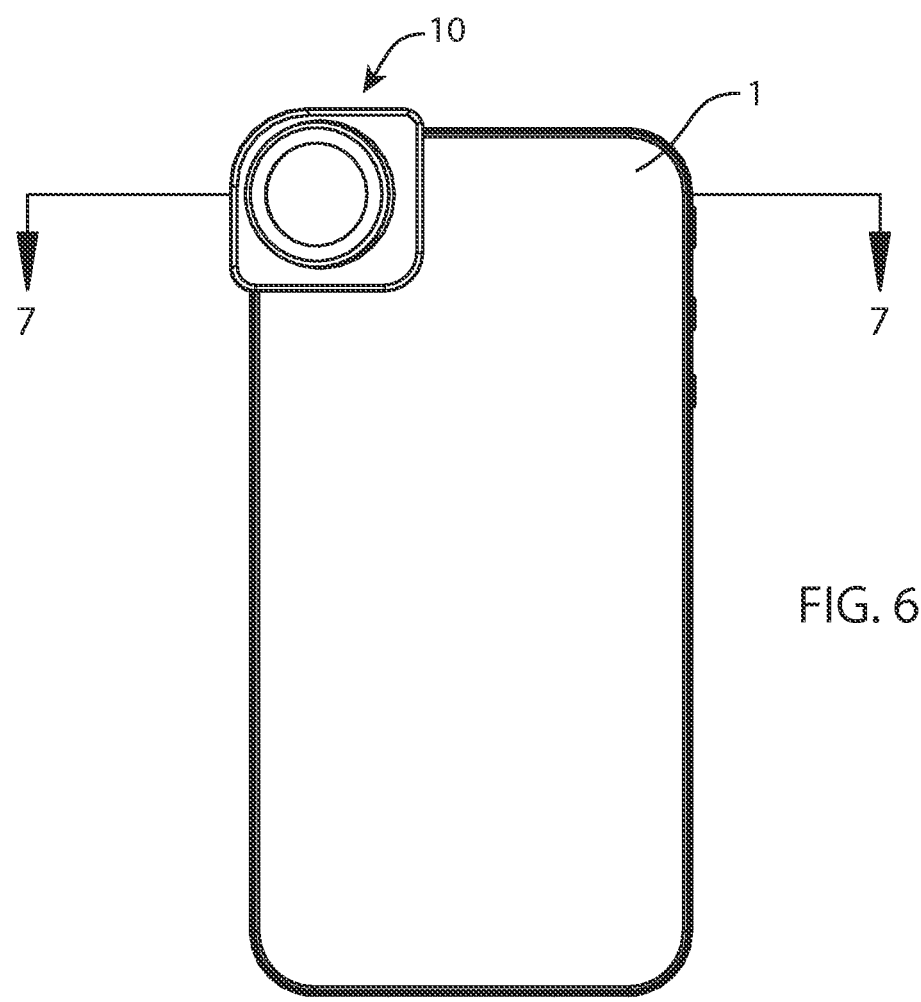
FIG. 6 is a bottom plan view of the engraved gemstone viewer shown in FIG. 1, mounted on an Apple® iPhone®.
Figure 9:
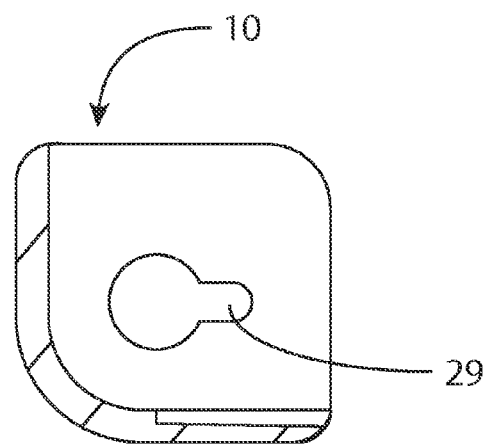
FIG. 9 is a side sectional view of the engraved gemstone viewer shown in FIG. 8, taken along line 9-9 of FIG. 8.
Figure 8:
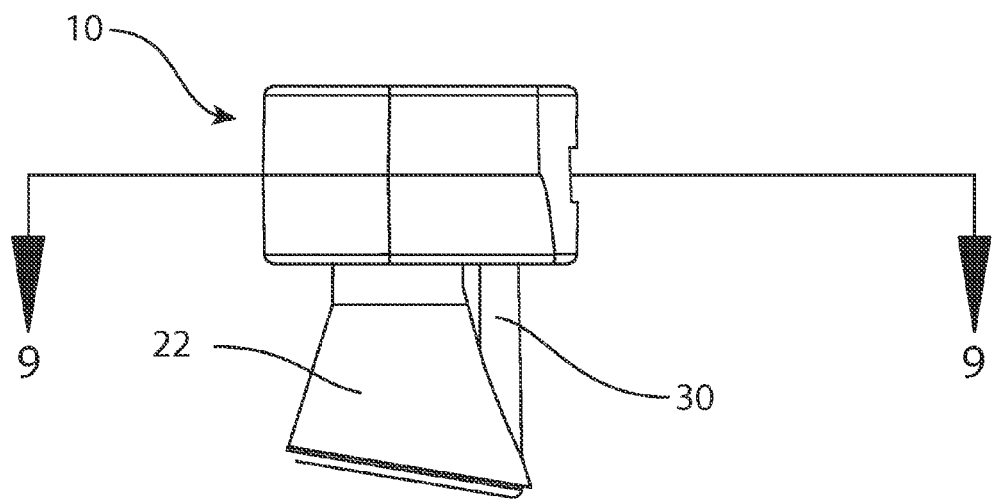
FIG. 8 is a side view of the engraved gemstone viewer.
Figure 10:
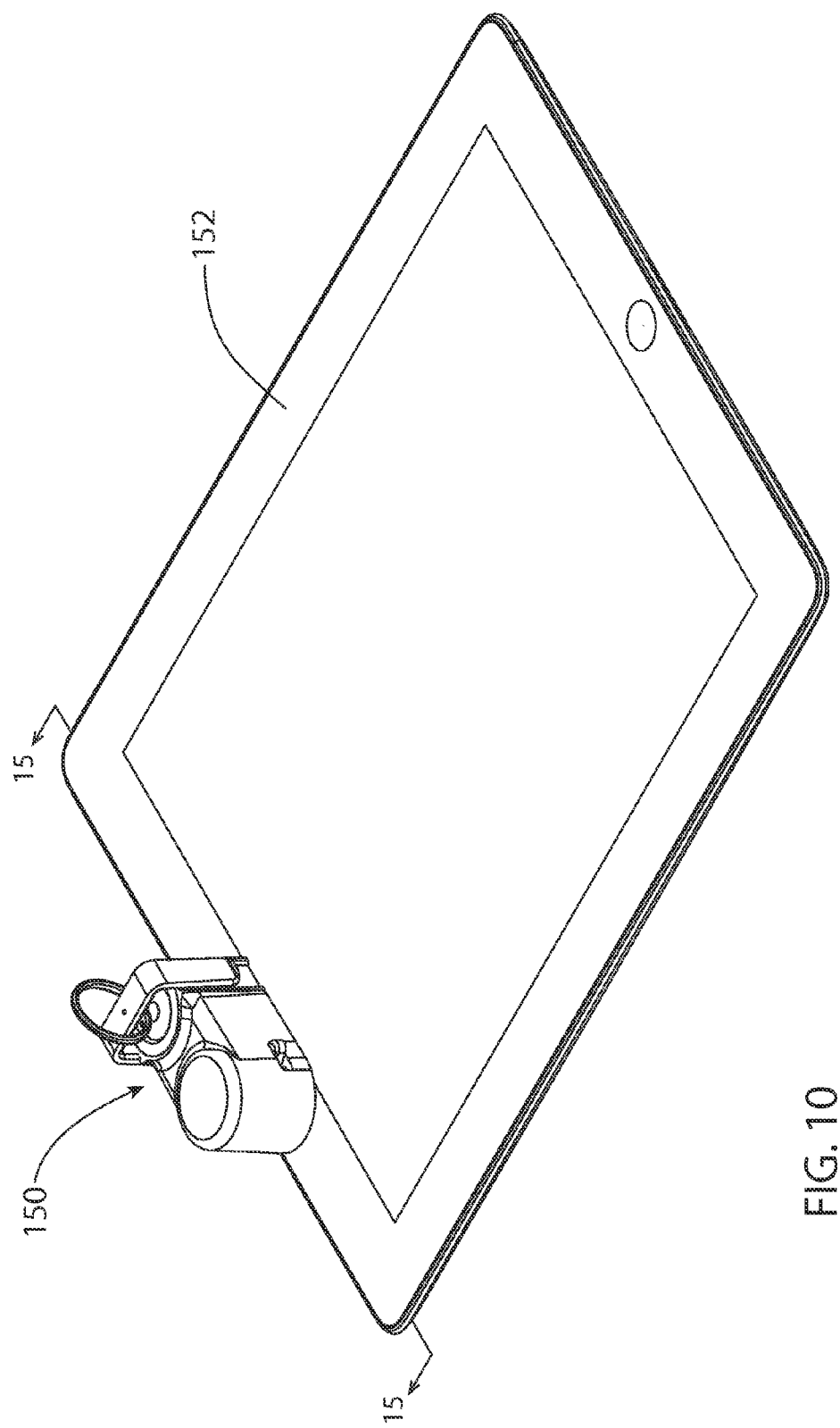
FIG. 10 is a perspective view of one embodiment of an engraved gemstone viewer according to the present invention, mounted on an Apple® iPad®.
Figure 11:
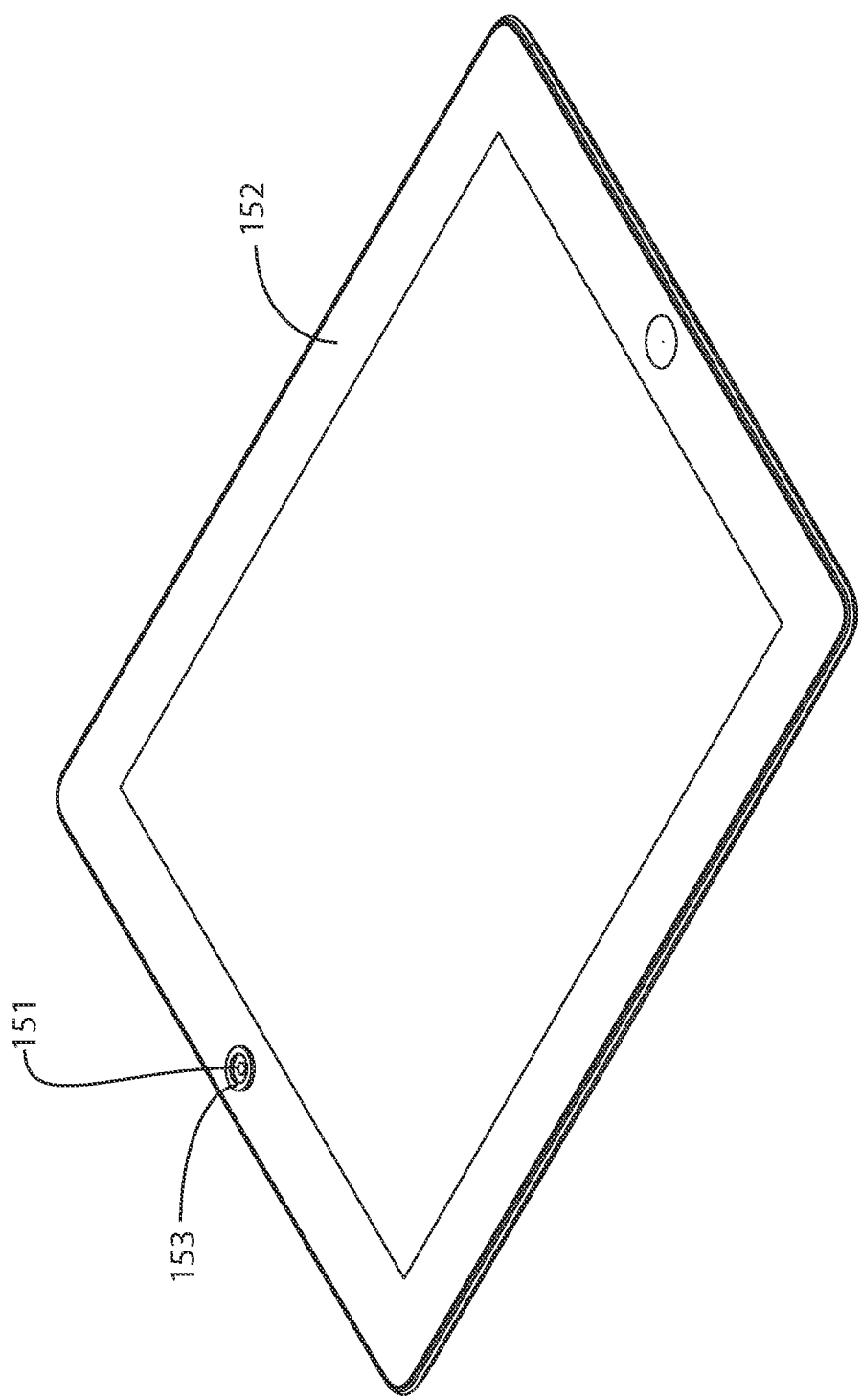
FIG. 11 is a perspective view of an alignment washer in accordance with the present invention, mounted on an Apple® iPad®.
Figure 14:
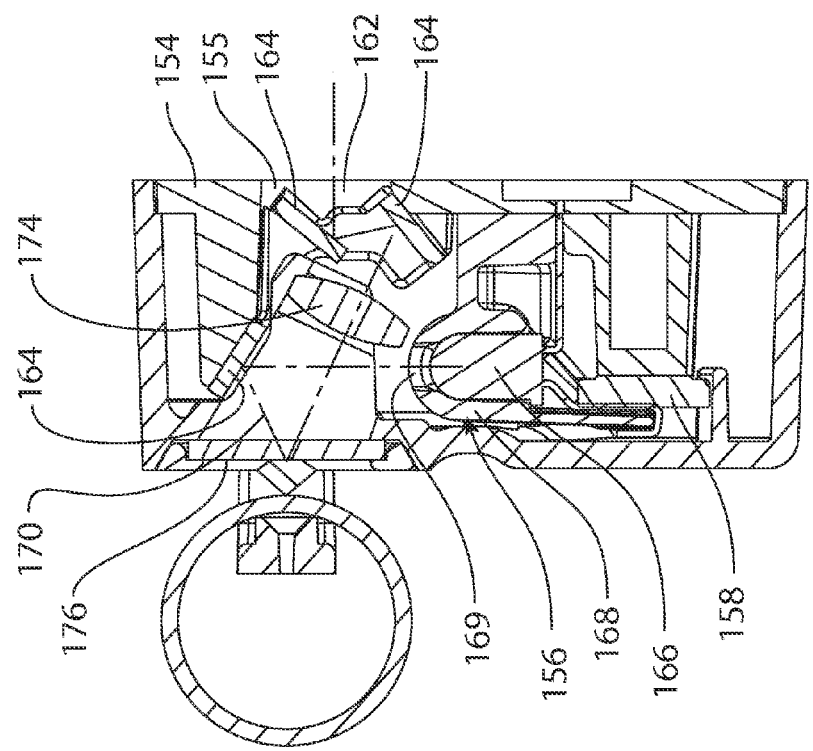
FIG. 14 is a section view of the engraved gemstone viewer of FIG. 10 taken generally along the line 14-14 in FIG. 13.

As shown in more detail in FIGS. 6-9, the opposite end of the viewer body 22 terminates at a plane, generally not parallel to the plane of the magnifying lens, where a focusing glass 26 is removably held in place by a removable retaining ring 28. The focusing glass 26 and the magnifying lens 24 are held at the correct distance from each other by the viewer body 22 such that the camera of the personal communications device 1 is properly focused through the magnifying lens at the top of the viewer body to the surface of a gemstone 3 (FIG. 5), such as a diamond, placed against the outside surface of the focusing glass at the bottom of the viewer body. The optimal angle for the plane of the focusing glass 26 compared to the plane of the magnifying lens 24 is determined by the focal length of the magnifying lens in relation to the location of the light source 4. In this embodiment, the angle would be between about 5 degrees and 25 degrees, and most preferably about 13 to 16 degrees.

The bottom plane 16 of the base 12 also has an opening 29 leading to a channel 30 to allow an unobstructed path for light from the light source 4 of the personal communications device 1 to pass through channel 30 oriented toward the focusing glass 26. As described above, then, the focusing glass 26 is oriented at an angle so the diamond 3 making contact with the focusing glass will receive the light beam path as directed to it from the light source 4 and reflect the light beam path back to, and through, the magnifying lens 24 to the camera lens 2 of the personal communications device 1.

In alternative embodiments, the path of the light source 4 could be oriented toward the magnifying lens so that the path of the light from the light source leads to the magnifying lens and then to the surface of the diamond 3, which in turn reflects the path of light back to, and through, the magnifying lens 24 to the lens 2 of the camera of the personal communications device. Such oriented paths of light beams, and the angles required, are disclosed in the Engraved Gemstone Viewer patents as referenced above.

FIGS. 12-19 show yet another embodiment of a gemstone viewer 150 in accordance with the invention. Unlike the embodiments described above that rely on a light source provided by the electronic communication device 1, the front facing cameras on typical tablet computers 152 do not include a light source. To overcome this limitation, gemstone viewer 150 includes an internal light source to provide the illumination necessary for the camera to take a useable photo of a gemstone 3. Of course, this embodiment may be used with any camera that does not have its own light source without departing from the invention.

Figure 15:
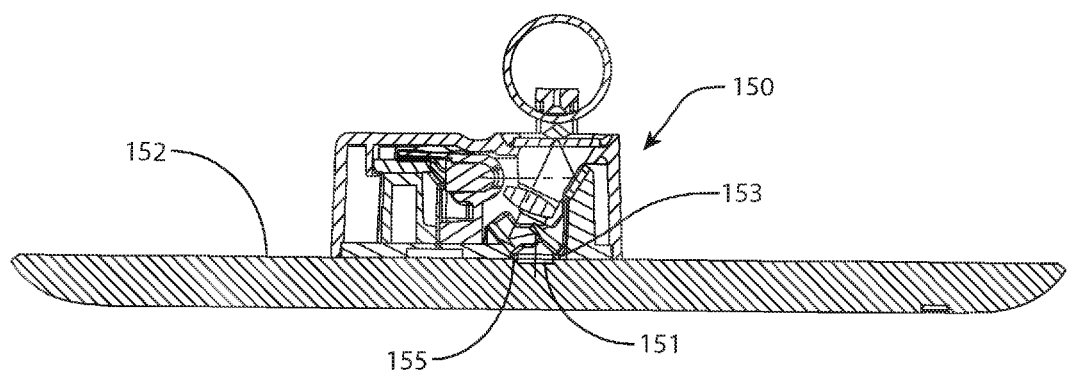
FIG. 15 is another section view of the engraved gemstone viewer of FIG. 10 taken generally along the line 15-15 in FIG. 10.

Gemstone viewer 150 includes a base 154 having an integral light source 156 powered by a battery 158, and controlled by a switch 160. The base 154 also includes a portal 162 that, when installed on the tablet computer, allows the front facing camera to view the inside of gemstone viewer 150. The base further includes a one or more mirrors 164 that direct light from the integral light source 156 through the gemstone 3 and then to the camera. As shown in FIG. 15, the integral light source 156 includes a lamp 166 and a lamp housing 168. The lamp housing 168 includes an opening 169 that directs a focused beam of light 170 toward one of the mirrors 164.

Figure 16:
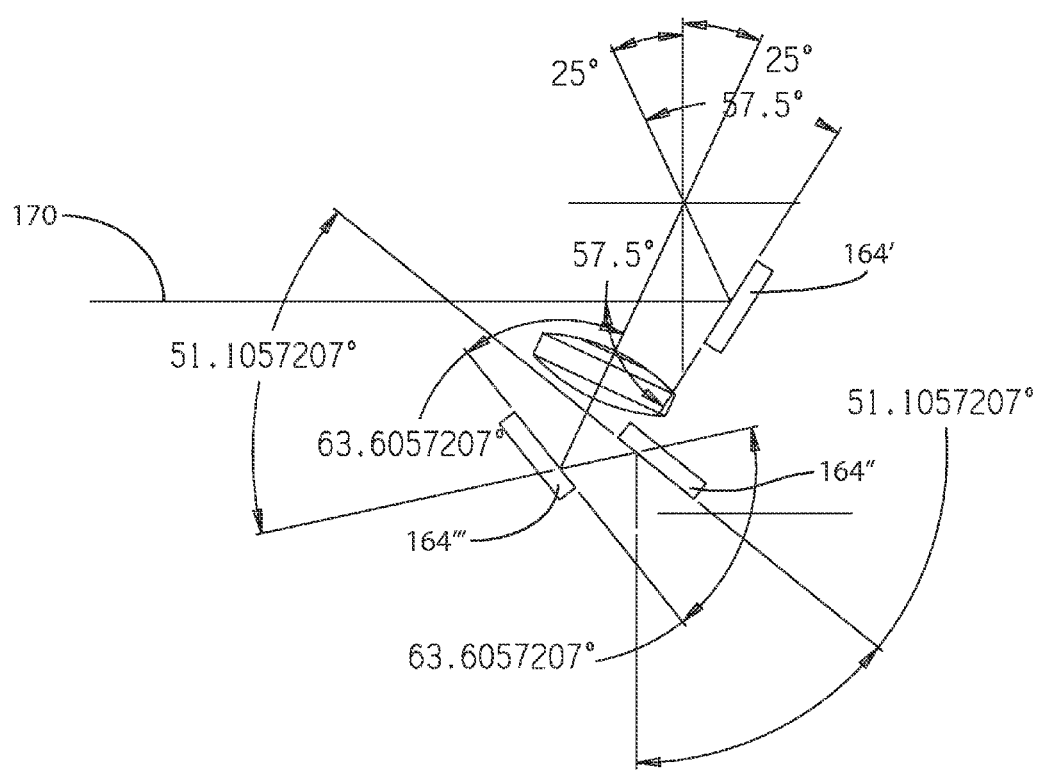
FIG. 16 is a schematic view of the engraved gemstone viewer of FIG. 10 showing the orientation of the lens and mirrors.
Figure 17:
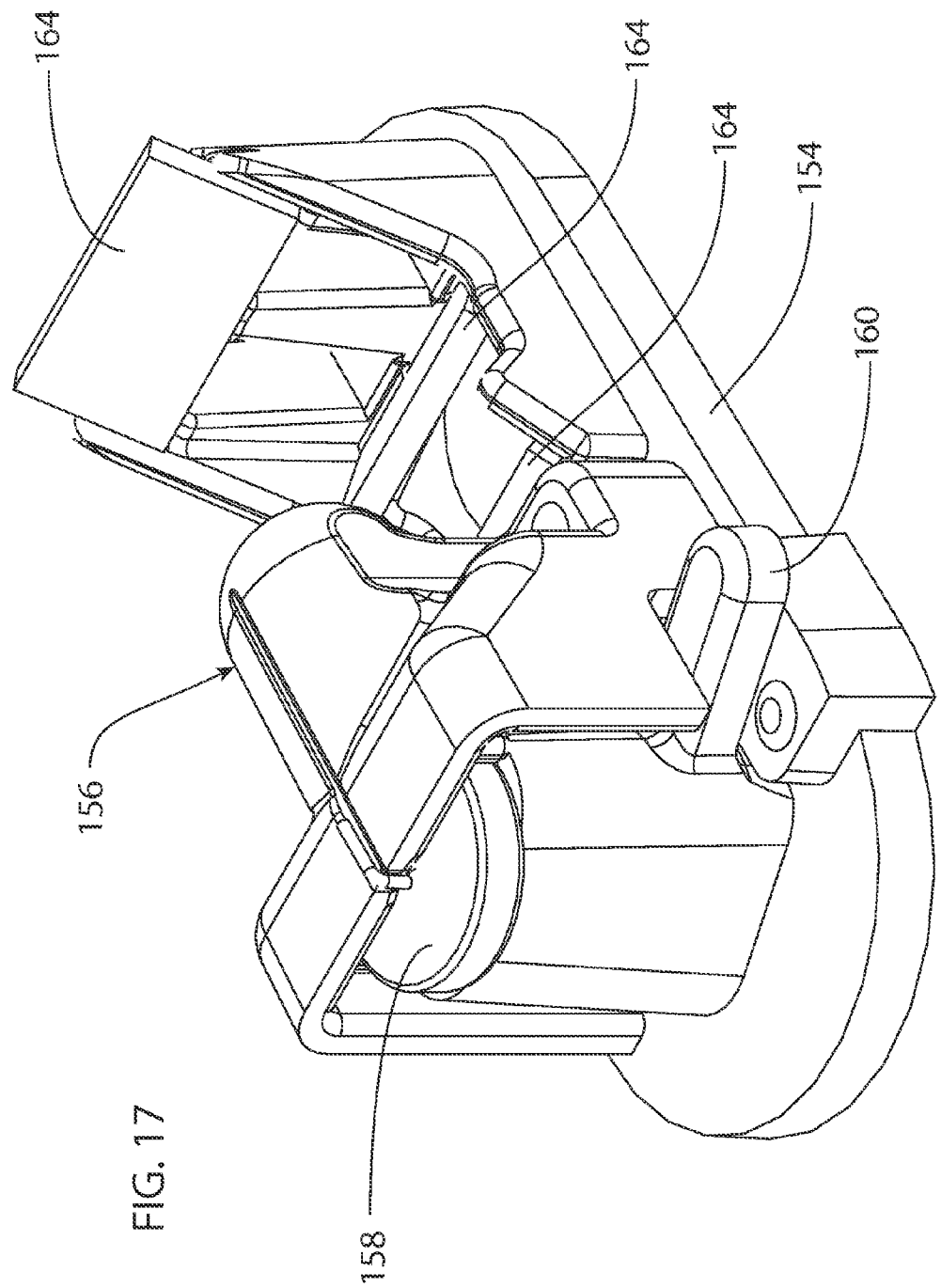
FIG. 17 is a perspective view of the base of the engraved gemstone viewer of FIG. 10.
Figure 19:
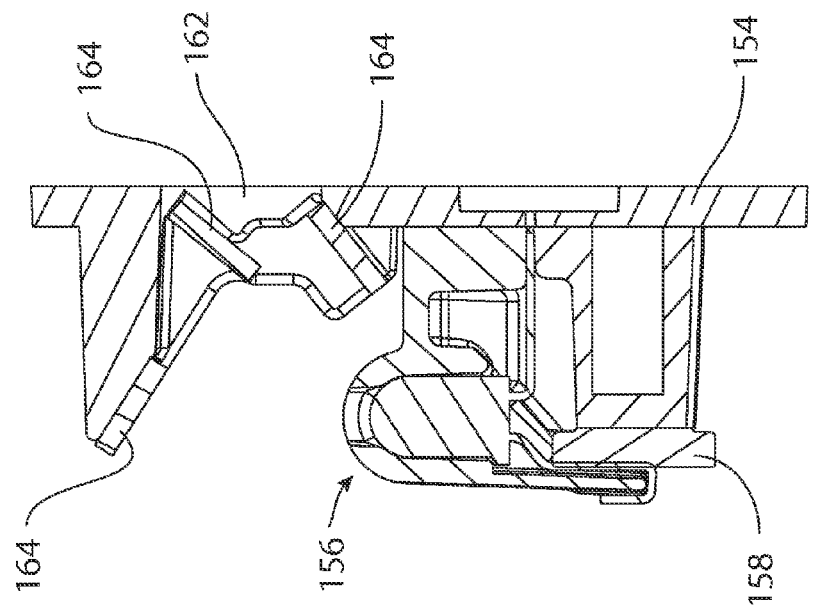
FIG. 19 is a section view of the base of FIG. 18 taken generally along the line 19-19 in FIG. 18.
Figure 18:
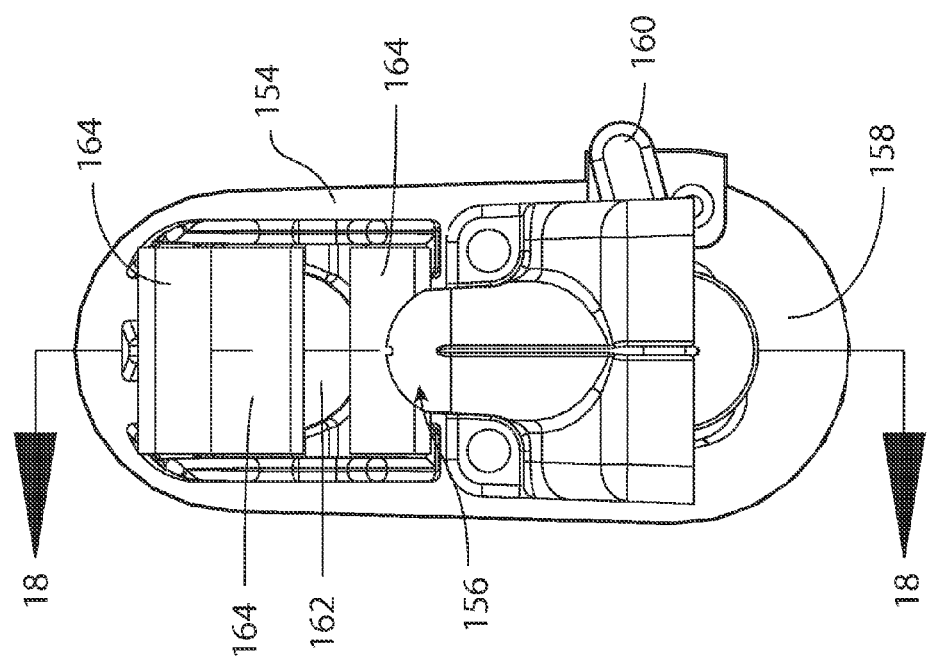
FIG. 18 is a top view of the base of FIG. 17.

FIG. 16 shows one embodiment of the mirrors 164 that directs the beam of light 170 from a horizontal path, to the gemstone 3, and finally to a vertical path to allow the camera 151, or alternatively the user's naked eye, to view the magnified and illuminated gemstone. As shown the beam of light 170 contacts a first mirror 164' disposed at a first angle from horizontal. The angles identified herein are preferred for the present embodiment, but any angles that result in a beam of light passing to a gemstone 3, a lens 174, and finally to an orientation correct to align with the camera lens, or alternatively the user's naked eye, may be used without departing from the invention. The embodiment shown in FIG. 16 shows the first angle is preferably an angle of 57.5°, which causes the beam of light to have an angle of incidence with the gemstone of 25°. After the beam of light 170 passes off the gemstone, it passes through a lens 174 before contacting a second mirror 164" that is disposed at an angle of about 63.6° from the path of light. Finally, the beam of light 170 reflects off of the second mirror 164" and contacts third mirror 164''', which is disposed at an angle of about 51.1° from the path of light after it reflects off of the second mirror.

In the embodiment shown, gemstone viewer 150 is aligned with a front facing camera 151 on a tablet computer 152. As shown, the gemstone viewer 150 is aligned with the front facing camera using an alignment washer 153. The alignment washer 153 is removably affixed to the tablet computer 152 so that the front facing camera 151 is centered inside the washer. The alignment washer 153 may be removably affixed to the tablet computer 152 by adhesive or any other suitable means. The gemstone viewer 150 includes an alignment recess 155 that aligns with the alignment washer 153 to axially align the portal 162 to the front facing camera 151. The gemstone viewer 150 will also work without an alignment washer 153 by simply manually aligning the portal 162 to the front facing camera 151.

One of the further advantages of this embodiment is that, besides being capable of being used with the front facing camera 151 of an electronic communications device that does not have its own light source, gemstone viewer 150 can also be used with the user's naked eye looking into the portal 162. This eliminates the need for a user to carry a portable electronic device with a camera. In either case, the gemstone viewer 150 allows the front facing camera 151 or the user's naked eye to read an inscription 202 (see FIG. 20) on the gemstone 3, which is otherwise invisible to the naked eye.

Figure 13:
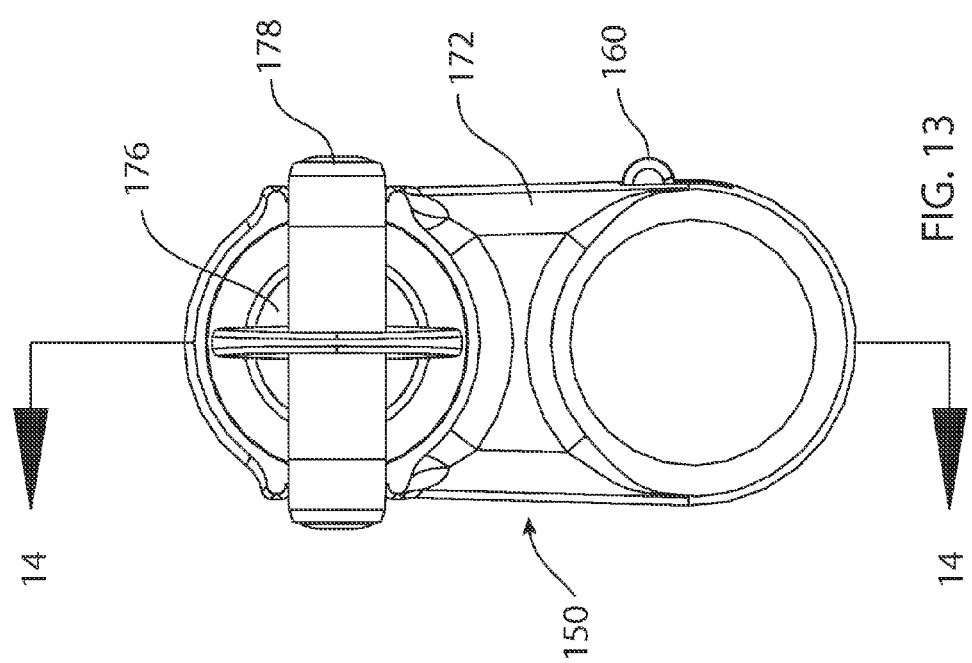
FIG. 13 is a top view of the engraved gemstone viewer of FIG. 10.

As shown in FIG. 13, a cover 172 is removably attached to the base 154. The cover 172 provides an enclosure that encloses and protects the integral light source 156 and the mirrors 164. Additionally, as shown in FIG. 15, the cover includes a lens 174 and a focusing glass 176, which is really any type of optically clear structure. As in the previously described embodiments, the focusing glass 176 and lens 174 are positioned to allow the front facing camera of the tablet computer 152 to focus on a gemstone placed on the focusing glass.

The embodiment shown also includes a gemstone retention clip 178 that secures a ring or loose gemstone 3 to the focusing glass 176. As shown, the gemstone retention clip 178 is removably attached to the cover 172, which allows rings and gemstones of varying sizes to be placed between the gemstone retention clip and the focusing glass 176. To secure a loose gemstone 3, gemstone retention clip 178 includes a recess 180 to accommodate the culet of a diamond. Of course, alternative recesses could be formed to accommodate other gemstone shapes without departing from the invention.

While this invention is susceptible of embodiment in many different forms, the drawings show and the specification describes only some of the preferred embodiments of the invention. It should be understood that the drawings and specification are to be considered an exemplification of the principles of the invention. They are not intended to limit the broad aspects of the invention to the embodiments illustrated. That function is left to the claims, which follow.

We claim:

1. A gemstone viewer for working with an electronic device having a camera lens, the gemstone viewer comprising:
    a base having an integral light source and a portal disposed in a bottom plane;
    one or more mirrors;
    a viewer lens;
    optically clear structure, with the viewer lens positioned between the optically clear structure and the camera lens;
    the optically clear structure and the viewer lens being held at a sufficient distance from each other such that the camera lens is properly focused through the viewer lens to the surface of a gemstone when the surface of the gemstone is placed against the optically clear structure; and
    the plurality of mirrors arranged to direct light from the integral light source off the surface of the gemstone to the camera lens.

2. The gemstone viewer of claim 1, wherein the base is removably secured to the electronic device.

3. The gemstone viewer of claim 1, further comprising a removable retaining ring for holding the optically clear structure in place, the optically clear structure being positioned to receive a gemstone on the optically clear structure.

4. The gemstone viewer of claim 1, further including a gemstone retention clip to secure a gemstone to the optically clear structure.

5. The gemstone viewer of claim 1, further including a cover associated with the base, wherein the viewer lens is connected to the cover.

6. The gemstone viewer of claim 1, wherein the integral light source is powered by a battery.

7. The gemstone viewer of claim 1, wherein the one or more mirrors are attached to the base.

8. The gemstone viewer of claim 1, further including a cover associated with the base, wherein the optically clear structure is connected to the cover.

9. A gemstone viewer for working with an electronic device having a camera lens, the gemstone viewer comprising:
    a base having an integral light source powered by a battery, the base having a portal disposed in a bottom plane;
    one or more mirrors attached to the base;
    a focusing glass, and a viewer lens positioned between the focusing glass and the camera lens;
    the focusing glass and the viewer lens being held at a sufficient distance from each other such that the camera lens is properly focused through the viewer lens to the surface of a gemstone when the surface of the gemstone is placed against the focusing glass; and
    the plurality of mirrors arranged to direct light from the integral light source off the surface of the gemstone to the camera lens.

10. The gemstone viewer of claim 9, wherein the base is removably secured to the electronic device.

11. The gemstone viewer of claim 9, further comprising a removable retaining ring for holding the focusing glass in place, the focusing glass being positioned to receive a gemstone on the focusing glass.

12. The gemstone viewer of claim 9 further comprising a cover associated with the base, the viewer lens and the focusing glass being connected to the cover, and being held at a sufficient distance from each other by the cover such that the camera lens is properly focused through the viewer lens to the surface of a gemstone when the surface of the gemstone is placed against the focusing glass.

13. The gemstone viewer of claim 12, wherein the cover further includes a gemstone retention clip to secure a gemstone to the focusing glass.

14. A gemstone viewer for use with an electronic device having a camera with a camera lens, the gemstone viewer comprising:
   a base having a portal disposed in a bottom plane;
   a light source positioned within the base;
   one or more mirrors positioned within the base;
   a cover, capable of fitting over the base;
   a viewer lens mounted within the viewer;
   a focusing glass connected to the cover, with the viewer lens positioned between the focusing glass and the camera lens when the cover is in position over the base;
   the focusing glass and the viewer lens being held at a sufficient distance from each other such that the camera lens is properly focused through the viewer lens to the surface of a gemstone when the surface of the gemstone is placed against the focusing glass; and
   the one or more mirrors arranged to direct light from the light source spectrally reflecting off the gemstone to the camera lens.

15. The gemstone viewer of claim 14, wherein the base is removably secured to the electronic device.

16. The gemstone viewer of claim 14, further comprising a removable retaining ring for holding the focusing glass in place.

17. The gemstone viewer of claim 14, wherein the cover further includes a gemstone retention clip to secure a gemstone to the focusing glass.

18. The gemstone viewer of claim 14, wherein the viewer lens is connected to the cover.

19. The gemstone viewer of claim 14, wherein the light source is powered by a battery.

20. The gemstone viewer of claim 14, wherein the one or more mirrors are mounted to the base.

* * * * *